United States Patent [19]

Anderson

[11] 4,179,816
[45] Dec. 25, 1979

[54] APPARATUS, METHODS AND INSTRUMENTS FOR REMOVING DENTAL RESTORATIONS

[76] Inventor: Grant W. Anderson, 932 Mullaghboy Rd., Glendora, Calif. 91740

[21] Appl. No.: 835,396

[22] Filed: Sep. 21, 1977

[51] Int. Cl.² .............................................. A61C 3/16
[52] U.S. Cl. .................................... 433/161; 433/218
[58] Field of Search ........................... 32/43, 44, 61, 46

[56] References Cited

U.S. PATENT DOCUMENTS 2,591,451   4/1952   Lynch et al. ............................ 32/43

FOREIGN PATENT DOCUMENTS 603210   9/1934   Fed. Rep. of Germany ............... 32/61

OTHER PUBLICATIONS

"Save a Crown with Remove a Crown" K & S Industries, P.O. Box 640152, Vieta, Florida, 33164.
"The Barlet Remover" Weber Dental Products, 7723 Fay Ave., Drawer 155P, La Jolla, Calif. 92037.

*Primary Examiner*—Robert Peshock
*Attorney, Agent, or Firm*—Benoit Law Corporation

[57] ABSTRACT

Disclosed methods and apparatus for removing a dental restoration from a tooth provide an aperture in the restoration and establish part of the restoration at the aperture as a shelf facing in the direction of the tooth. A force acting on the shelf relative to and away from the tooth is established at the provided aperture and the restoration is removed from the tooth with the force. In practice, the shelf may be established by undercutting the restoration at the aperture.

18 Claims, 14 Drawing Figures

APPARATUS, METHODS AND INSTRUMENTS FOR REMOVING DENTAL RESTORATIONS

BACKGROUND OF THE INVENTION

1. Field of the Invention

The subject invention relates primarily to the art of dentistry and, more specifically, to methods, apparatus and instruments for removing bridges, full and partial crowns, inlays, including one and two surface inlays, onlays and similar dental restorations from patients' teeth without injury to or impairment of such teeth and, typically, without injury to the removed restoration.

2. Prior Art Statement

A well-known type of crown and bridge remover uses a pair of tongs for gripping a crown or bridge abutment. In one form of execution, one of the tongs is provided with an aperture for accommodating a hook with which forces are exerted on the remover by the dentist. In practice, the dentist frequently has to exert a hammering action on that type of remover to make it work. For this purpose, there exists an inertia type of hammer with which the remover with engaged crown or bridge is hammered away from the teeth.

Unfortunately, such harsh procedure often eventuates dislocation of, damage to or even loss of the underlying tooth.

Another tong-type of crown and bridge remover employs a threaded pin which is brought to bear upon the tooth through a hole drilled into the occlusal surface of the crown or bridge abutment to be removed.

In practice, this remover, as well as the other tong-type remover previously mentioned herein, is restricted in its utility to the removal of full crowns or bridge abutments which can be firmly gripped by a pair of tongs. Even then, the necessity of the tong having to establish a firm grip at the cervical portion of the crown often eventuates damage to the gum or tooth at the cervical line or discomfort to the patient.

Another kind of remover which does not rely on a tong-type engagement comprises a conical screw with a hexagonal or square head and a wrench for engaging that head. A hole suitable for tapping by the screw is drilled into the occlusal surface of the crown to be removed. A thread is then cut into the crown at the hole with the screw actuated by the wrench. In the course of the threading operation the tip of the screw will come to bear on the underlying tooth and further turning of the screw tends to lift the crown away. An advantage of this procedure is that it can be used not only on crowns, but also on inlays which could not be gripped by tongs.

However, the utility of the latter screw-type remover is still limited to relatively heavy crowns and inlays of sufficient thickness to permit an effective thread cutting action by the screw. Also, the necessarily relatively sharp tip of the conical tapping screw has a tendency to split or otherwise damage the underlying tooth structure.

In consequence, there are many situations wherein resort has to be had to one of the cruder procedures for removing bridges, crowns, inlays and onlays, involving the use of hook-like or other force-applying instruments and hammers, frequently damaging the underlying tooth or otherwise discomforting the patient.

SUMMARY OF THE INVENTION

It is a broad object of this invention to overcome the above mentioned disadvantages.

It is a related object of this invention to provide improved methods, apparatus and instruments for removing dental restorations, such as bridges, crowns, inlays and onlays.

It is a related object of this invention to provide improved methods, apparatus and instruments for increasing the dentist's convenience and the patient's comfort, and of preserving the integrity of the patient's teeth in the course of dental restoration work.

Other objects of this invention will become apparent in the further course of this disclosure.

From a first aspect thereof, the subject invention resides in a method of removing a dental restoration from a tooth, comprising in combination the steps of providing an instrument with lateral projection means at a lower portion thereof, providing an aperture in and through the restoration, extending said aperture into an oblong shape in a face of the restoration by providing said aperture with a sufficient first width in said restoration for a reception of said projection means therethrough, and a second width extending in the same plane as said first width at an angle to said first width and being too small to receive said projection means, establishing part of the restoration at the aperture as a shelf facing in the direction of the tooth by undercutting the restoration at said aperture in extension of said second width, inserting said lower portion of the instrument into said oblong aperture, with said lateral projection means being oriented in alignment with said first width of said oblong aperture and being inserted to below said dental restoration, rotating said lateral projecting means for moving said lateral projecting means to below said shelf, establishing at the aperture with said lateral projection means a force acting on the shelf relative to and away from the tooth, and removing the restoration from the tooth with said force.

From another aspect thereof, the subject invention resides in a method of removing from a tooth a dental restoration located on dental matter including said tooth, comprising in combination the steps of providing an aperture in the restoration, extending said aperture into dental matter adjacent the restoration, establishing at the aperture a force acting on the restoration and between a wall of said aperture in the restoration and a side wall of said extended aperture in dental matter, and removing the restoration from the tooth with said force.

From another aspect thereof, the subject invention resides in a method of removing from a tooth a dental restoration having a side wall and being located on said tooth, comprising in combination the steps of providing in said side wall of the dental restoration and in an adjacent portion of said tooth an aperture having a first land located on a top portion of said aperture in the restoration and a second land located on a bottom portion of the aperture in said tooth, establishing at the aperture a force acting on the restoration and between the first and second lands, and removing the restoration from the tooth with said force.

From another aspect thereof, the subject invention resides in a method of removing a dental restoration from a tooth, comprising in combination the steps of providing an instrument with lateral projections at a lower portion thereof providing an aperture in and through the restoration, extending said aperture into an oblong shape in a face of the restoration by providing said aperture with a sufficient first width in said restoration for a reception of said projections therethrough, and a second width extending in the same plane as said first width at an angle to said first width and being too small to receive said projections establishing a first portion of the restoration at the aperture as a first shelf facing in the direction of the tooth, and a second portion of the restoration across the aperture from the first part as a second shelf facing in the direction of the tooth by undercutting the restoration at said aperture in extension of said second width, inserting said lower portion of the instrument into said oblong aperture, with said lateral projections being oriented in alignment with said first width of said oblong and being inserted to below said dental restoration, rotating said instrument for moving said lateral projections to below said shelves, establishing at the aperture with said lateral projections forces acting on the first and second shelves relative to and away from the tooth, and removing the restoration from the tooth with said forces.

From another aspect thereof, the subject invention resides in a method of removing a dental restoration from a tooth with the aid of an instrument having a first part and a second part, comprising in combination the steps of providing said first part with a lateral projection providing an aperture in and through the restoration for receiving the first and second parts, extending said aperture into an oblong shape in a face of restoration by providing said aperture with a sufficient first width in said restoration for a reception of said first and second parts along with said lateral projection, and a second width extending in the same plane as said first width at an angle to said first width and being too small to receive said lateral projection along with the first and second parts, undercutting the restoration at the aperture in extension of said second width, inserting the first part with lateral projection and the second part into the aperture through said first width and moving the projection of the first part into line with the second width and under the undercut restoration, and moving the inserted second part against the tooth and relative to the first part to remove the restoration from the tooth.

From another aspect thereof, the subject invention resides in a method of removing from a tooth with the aid of an instrument, having a first part and a second part, a dental restoration having a side wall and being located on said tooth, comprising in combination the steps of providing an aperture in said side wall of the restoration and in a portion of said tooth adjacent the restoration, and providing said aperture with a first land located on a top portion of said aperture in the restoration and a second land located on a bottom portion of the aperture in said tooth, engaging the restoration at said first land of the aperture with the first part of said instrument, and moving the second part of said instrument against said tooth at said second land of the aperture and relative to the first part to remove the restoration from the tooth.

From another aspect thereof, the subject invention resides in a method of removing from a tooth with the aid of an instrument, having a first part and a second part, a dental restoration located on dental matter including said tooth, comprising in combination the steps of providing in said dental matter and said dental restoration an aperture and, respectively, first and second lands facing each other across said aperture, engaging the restoration at the second land adjacent the aperture with the first part and dental matter at the first land adjacent the aperture with the second part, and relatively moving the engaged first and second parts to remove the restoration from the tooth.

From another aspect thereof, the subject invention resides in a method of removing a dental restoration from a tooth with the aid of an instrument having a first part and a second part, said dental restoration being affixed to said tooth by a cement layer, comprising in combination the steps of providing the first part of the instrument with lateral projections extending in opposite directions and corresponding in thickness to said cement layer, providing the restoration with an aperture having a first width for receiving the first and second parts along with said lateral projections, and having a second width extending at an angle to the first width and being too small to receive said lateral projections along with the first and second parts, undercutting the restoration in extension of the second width, inserting the first part with said lateral projections and the second part through the first width of the aperture, positioning the lateral projections under the undercut restoration at opposite extensions of the second width of the aperture, moving the inserted second part against the tooth and the positioned lateral projections into engagement with the restoration, and removing the restoration from the tooth by relatively moving the inserted first and second parts relatively to each other.

From another aspect thereof, the subject invention resides in a dental instrument for removing from a tooth a partial crown having a side wall and an aperture extending into the tooth, comprising in combination, a first part having a lateral projection extending to the approximate thickness of said partial crown for the partial crown at the aperture, a second part extending through said first part for engaging the tooth at the aperture and having thread means engaging said first part, and means connected to the first and second parts for rotating the second part relative to the first part while maintaining said first part against rotation whereby to remove the restoration from the tooth.

From another aspect thereof, the subject invention resides in a combination of dental matter including a tooth, a dental restoration located on said dental matter and having an aperture extending into said dental matter, and a dental instrument for removing the restoration from the tooth, including a first part engaging the dental restoration at the aperture, a second part engaging dental matter at the aperture, and means connected to the first and second parts for moving the first and second parts relatively to each other whereby to remove the restoration from the tooth.

From another aspect thereof, the subject invention resides in a combination of dental matter including a tooth and having a first land, a dental restoration located on the dental matter and having a second land, said dental matter and dental restoration having an aperture adjacent said first and second lands, and a dental instrument for removing the restoration from the tooth, including a first part engaging the restoration at the second land, a second part engaging dental matter at the first land, and means connected to said first and second parts for moving said first and second parts relatively to each other to remove the restoration from the tooth.

From another aspect thereof, the subject invention resides in a combination of dental restoration located on a tooth and having an undercut aperture, and a dental instrument for removing the restoration from the tooth, including a first part inserted in the aperture and having opposite lateral projections engaging the restoration at the undercut aperture, a second part inserted in the aperture and engaging the tooth, and means connected to the first and second parts for moving the first and second parts relatively to each other to remove the restoration from the tooth.

From another aspect thereof, the subject invention resides in a dental instrument for removing from a tooth a dental restoration affixed to said tooth by a cement layer and having an oblong aperture of a first width and a second width extending in the same plane as the first width at an angle to and being smaller than said first width comprising, in combination, means for establishing at the aperture a force acting on the restoration in a direction away from the tooth, including a first part insertable into the aperture and having lateral projections corresponding in thickness to said cement layer and having an overall dimension smaller than said first width and larger than said second width for insertion of said first part and lateral projections through said oblong aperture in alignment with said first width and for engaging the restoration upon alignment of said lateral projections with said second width after insertion of said lateral projections to below the restoration, a second part extending through said first part for engaging said tooth below said restoration and having thread means engaging said first part, and means connected to the first and second parts for rotating the second part relative to the first part while maintaining said first part against rotation to remove the restoration from the tooth.

BRIEF DESCRIPTION OF THE DRAWINGS

The subject invention and its various objects and aspects will become more readily apparent from the following detailed description of preferred embodiments thereof, illustrated by way of example in the accompanying drawings, in which like reference numerals designate like or functionally equivalent parts and in which.

DESCRIPTION OF PREFERRED EMBODIMENTS

Figure 1:
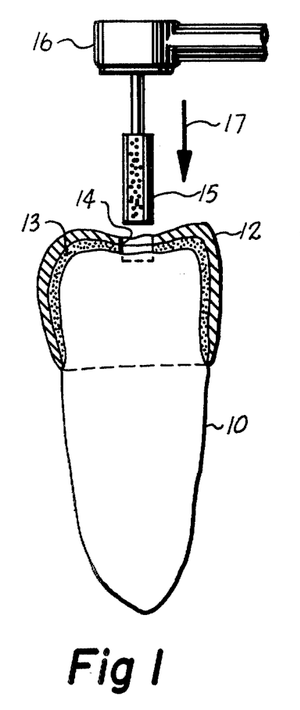
FIG. 1 is a mesial aspect of a tooth with dental restoration and a side view of a first dental instrument employed preparatory to a removal of the restoration.
Figure 2:
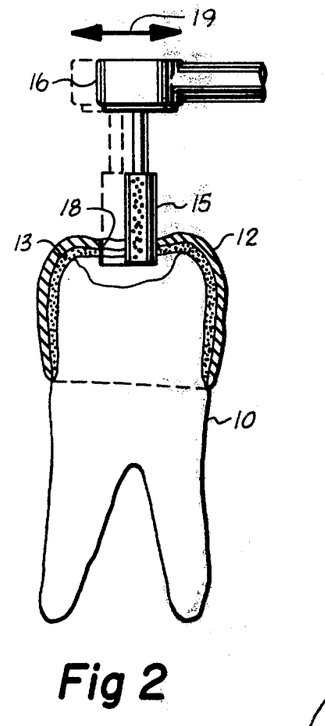
FIG. 2 is a buccal aspect of the tooth shown in FIG. 1 together with a showing of a second phase of the operation of the first dental instrument on the tooth and restoration in accordance with a preferred embodiment of the subject invention.

The tooth 10 shown in FIGS. 1 to 5 has a dental restoration 12 attached or bonded thereto by a cement layer 13. As seen in FIGS. 1 and 2, the dental restoration 12 may be a crown, such as a full crown. However, it is to be understood that the methods, apparatus and instruments of the subject invention are also suitable for removing bridges, partial crowns, one or two surface inlays and onlays. Accordingly, the dental restoration 12 seen in FIGS. 3, 5 and 7 may, for instance, be a full crown, partial crown, inlay or onlay or a bridge abutment.

Also, while FIGS. 1 and 2 depict a molar or premolar, the dental restoration removing methods, apparatus and instruments according to the subject invention are also operative on canine teeth and incisors.

Preparatory to a removal of the dental restoration 12, a hole 14 is drilled through a central portion of the restoration. As shown in FIG. 1, a drill or burr 15, driven by a turbine 16 may be employed for this purpose. In the preferred embodiment shown in FIG. 1, the drill 15 is moved in the direction of the arrow 17 towards, onto and through the occlusial surface of the restoration 12.

According to FIG. 1, the hole 14 is drilled not only through the occlusial part of the restoration 12, but also through the cement 13 and into a top portion of the tooth 10 into or through the enamel, if such is still present on the tooth structure, and into part of the dentine, as necessary. The term "cement" as herein employed refers broadly to any adhesive or bonding substance with which the restoration to be removed is attached to the tooth structure. This "cement" is, of course, different from the natural cement or cementum situated on the root surfaces of teeth.

Extending the hole 14 into the tooth may not always be necessary. For instance, the layer of cement 13 may be sufficiently thick in a given situation to permit performance of the entire undercutting function hereafter to be described in the cement layer itself. Also, the requisite undercutting operation may extend into part of the dental restoration itself if the thickness of restoration permits such undercutting and if it is desired not to cut into the tooth itself. The expression "dental matter" is herein employed as a generic term for the tooth and cement or other adhesive located between the tooth and the restoration. Accordingly, the hole 14 may be said to extend from the restoration into "dental matter", signifying either the layer of cement 13 or the tooth 10 or both such layer and tooth, with or without natural enamel layer and underlying dentine structure.

Whether the dental restoration is made of gold or any other metal or material, the types of drills available in a dental office are usually adequate for the drilling of the hole 14 and for the operation presently to be described in conjunction with FIG. 2.

Both FIGS. 1 and 2 show the dental restoration 12 and underlying layer of cement 13 in section for ease of illustration.

Figure 4:
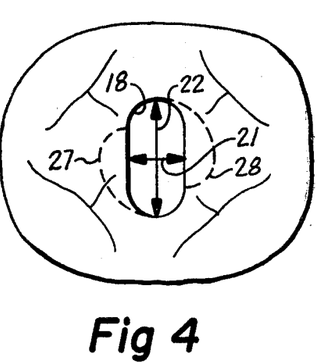
FIG. 4 is an occlusial aspect, on an enlarged scale, of the dental restoration and tooth prepared according to FIGS. 1 to 3.

According to the buccal aspect of FIG. 2, the hole 14 is laterally extended into an oblong shape or aperture 18 in a face of the restoration as seen also in the occlusial aspect of FIG. 4.

To this end, and as shown in FIG. 2, the turbine 16 with rotating drill 15 is moved mesially and distally or back and forth as indicated by the double-headed arrow 19 in FIG. 2. The original width of the hole 14 is thereby preserved in a buccal and lingual direction as seen in FIG. 4 where a double-headed arrow 21 designates a certain dimension or width of the oblong aperture 18 corresponding to the diameter of the initially drilled hole 14. On the other hand, a double-headed arrow 22 in FIG. 4 designates the larger dimension, width or length of the oval aperture 18 obtained by action of the drill 15 as shown in FIG. 2. For practical purposes, the dimension 22 of the aperture 18 may be considered a first width and the dimension 21 a second width extending in the same plane as said first width at an angle to and being smaller than the first width 22.

Figure 3:
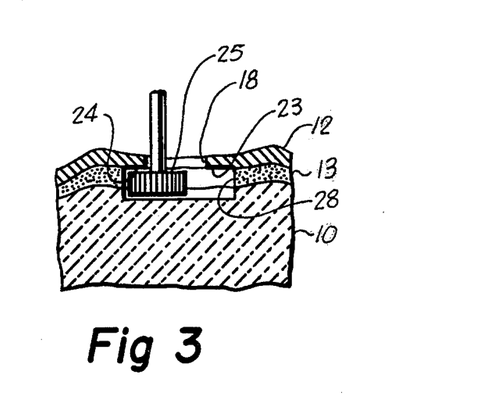
FIG. 3 is a detail view, on an enlarged scale, of the mesial aspect of FIG. 1, together with a side view of part of a second dental instrument employed in accordance with a preferred embodiment of the subject invention in preparing the tooth for a removal of the dental restoration.

As shown in FIGS. 3 and 4, the restoration 12 is undercut at the aperture 18 in extension of the smaller second width to establish part of the restoration 12 as shelves or lands 23 and 24 facing in the direction of the tooth 10.

As seen in FIG. 3, a dental cutting wheel 25 is employed and may be driven by the turbine 16, shown in FIGS. 1 and 2, to undercut parts of the restoration 12 at the aperture 18 in extension of the smaller width 21. The cutting wheel 25 is moved into the dental matter at both sides of the aperture 18 to form lateral pockets 27 and 28 shown by dotted lines in FIG. 4.

Figure 5:
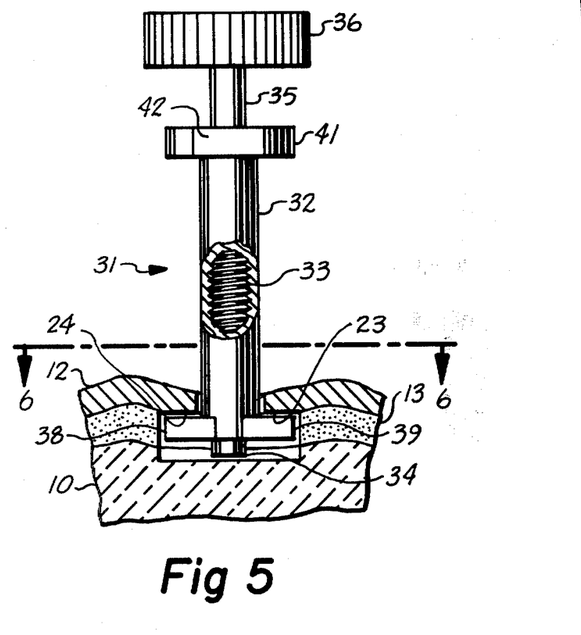
FIG. 5 is a detail view similar to FIG. 3, together with an elevation of an inserted dental restoration removing instrument according to a preferred embodiment of the subject invention.
Figure 6:
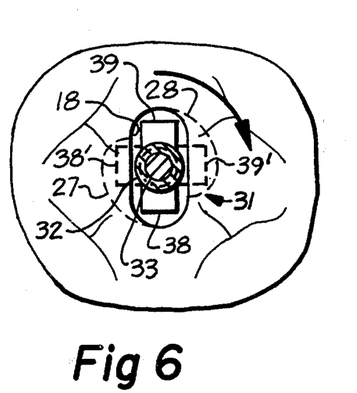
FIG. 6 is an occlusial aspect similar to FIG. 4, taken along the line 6—6 of FIG. 5 and showing actuation of the dental instrument shown in FIG. 5 from a first to a second position.
Figure 7:
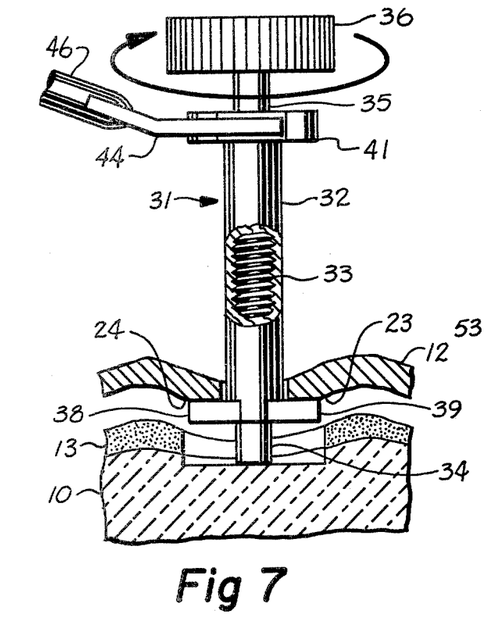
FIG. 7 is a view similar to FIG. 5 showing actuation of, and removal of the restoration by, the inserted dental instrument of FIG. 5.

The oblong aperture 18 and undercut lateral pockets 27 and 28 having been formed as shown in FIGS. 1 to 4, the restoration 12 is thereupon removed from the tooth 10 as shown in FIGS. 5 to 7 by a dental restoration removing instrument 31. That instrument 31 has an internally threaded sleeve or casing 32 with a screw 33 being threaded in and extending longitudinally of the sleeve 32 to project with a tip 34 from the lower end of the sleeve 32. The screw 33 also has a shaft 34 which may be integral with the threaded part but which, projecting from the upper end of the sleeve 32, need not itself be threaded. A knurled knob 36 is attached to the top of the shaft 35 to act as a manually engageable part for rotating the screw 33 in the threaded sleeve 32.

The lower part of the sleeve 32 has lateral projections 38 and 39. In the preferred embodiment illustrated in FIGS. 5 to 7, the projections 38 and 39 extend laterally of the sleeve 32.

The diameter of the hole 14 and thus the second width of the aperture 18 are too small as to be able to receive the sleeve 32 with projections 38 and 39. Conversely, the first width 22 of the oblong aperture 18 is sufficiently dimensioned to receive the projections 38 and 39 therethrough.

Accordingly, the lower portion of the instrument 31, including the lower portion of the sleeve 32 with projections 38 and 39 and the lower portion or tip 34 of the screw 33, having an overall dimension smaller than said first width 22 and larger than said second width 21, is inserted into the aperture 18, with the projections 38 and 39 being oriented in alignment with the larger width 22. While the tip 34 for illustrative purposes has been shown in FIG. 5 and even may project slightly from the sleeve during insertion of the dental instrument 31 in the aperture 18, it preferably is even with or located inside of the sleeve 32 during such insertion.

This insertion of the lower instrument portion with projections 38 and 39 proceeds into the extension of the aperture 18 below the dental restoration 12.

The dental instrument 31 with lateral projections 38 and 39 is thereupon rotated about its longitudinal axis for moving the projections 38 and 39 into the pockets 27 and 28 below shelves 23 and 24. In particular, the casing 32 with inserted screw 33 may be rotated and the lateral projections 38 and 39 angularly moved from alignment with the first width 22 into alignment with the second width 21, whereby each projection moves through an angle which corresponds to the angle between the widths 21 and 22. In FIG. 4, this angle, by way of example, is a right angle and the inserted instrument 31 is, accordingly, rotated by an angle of 90° as shown in FIG. 6, whereby the projections 38 and 39 are moved to the diametrically opposed positions 38' and 39' in the lateral undercut pockets 27 and 28 below the shelves 23 and 24 of the restoration 12.

Preferably, when the dental restoration 12 is undercut as shown in FIG. 3, the shelves 23 and 24 are provided as diametrical extensions of the smaller second width 21. The lateral pockets 27 and 28 may be cut in the form of lobes which from opposite ends of the oblong aperture 18 follow a radius centered at the intersection of the widths 21 and 22 and equal in length to one half the first width 22. The lobes of the pockets 27 and 28 preferably follow such a curve for an arc sufficient to permit the above mentioned rotation of the dental instrument 31.

At that point, each of the lobes preferably terminates in a curve of smaller radius forming stops for the angularly moved projections 38 and 39. As seen in FIG. 6 the angular movement of the projections 38 and 39 is stopped at the positions 38' and 39' by the configuration of the pockets 27 and 28.

In practice, the casing 32 and especially the projections 38 and 39 are preferably formed of high-grade steel or an essentially equivalent material, which permits the height of the projections 38 and 39 to be as small as possible, corresponding in thickness to the cement layer 13 so that the extension of the aperture 18 into the dental structure need not proceed to a depth coming close to the pulp chamber in the case of a live tooth.

The insertion and rotation of the lower instrument portion including the projections 38 and 39 having been completed, the knob 36 is rotated relative to the sleeve 32 whereby the tip 34 of the screw 33 is moved into engagement with the tooth 10 or other dental matter below aperture 18. In particular, the mutually engaging threaded portions of the sleeve 32 and screw 33 translate rotary motion of the knurled knob 36, which may be manually effected by the dentist, into translatory motion of the screw 33 so that the tip 34 moves toward and engages the dental matter inside the cut chamber below the aperture 18. Concurrently, rotation of the knob 36 also effects engagement of the projections 38 and 39 with the restoration at the shelves 23 and 24 as shown in FIG. 7.

Rotation of the knob 36 and shaft 35 relative to the sleeve 32 is continued until the restoration 12 is lifted from the tooth structure by increasing movement of the tip portion 34 away from the lower extremity of the sleeve 32 and projections 38 and 39. In this manner, the bond between the restoration 12 and the tooth structure is broken whereby the restoration may be removed from the tooth. As indicated in FIG. 7, such break occurs at the layer of cement 13 with which the restoration 12 was originally attached to the tooth 10.

As already indicated above, the projections 38 and 39 may be stopped or restrained in their positions 38' and 39' against further rotation by the illustrated shape of the undercut lateral pockets 27 and 28. In practice, such restraint may be supported or even replaced by a restraint exerted on the instrument sleeve 32 itself.

Figures 8, 9, 10, 12:
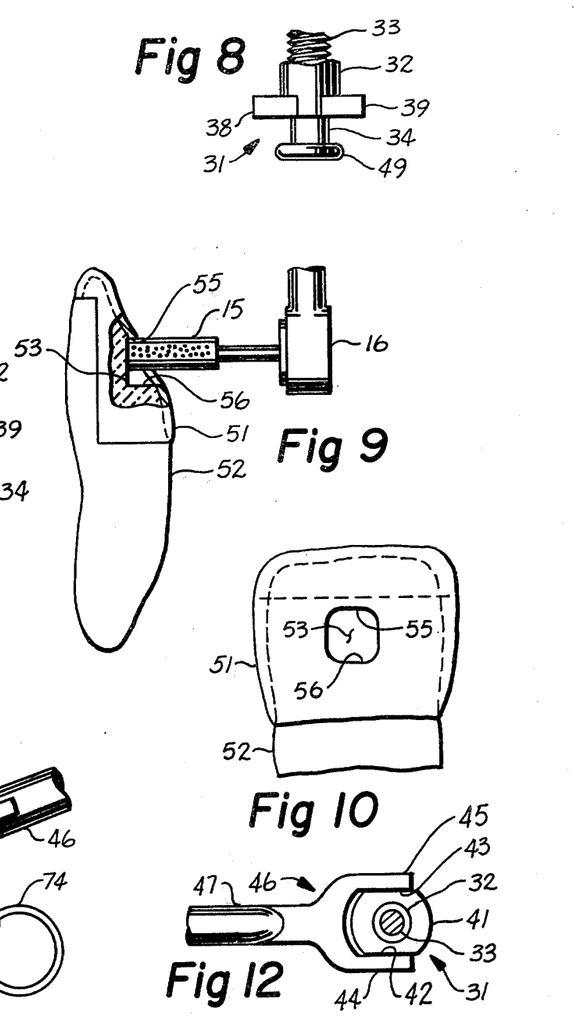
FIG. 8 is a fractional view of a detail of FIG. 7 showing a modification, in accordance with a further preferred embodiment of the subject invention, of the dental restoration removing instrument.
FIG. 9 is a buccal aspect of a further tooth having a dental restoration, together with a side view of a first dental instrument employed in accordance with a further preferred embodiment of the subject invention in preparing the tooth for a removal of the dental restoration.
FIG. 10 is a mesial aspect of the tooth and prepared dental restoration shown in FIG. 9.
FIG. 12 is a fractional view of a wrench and of a section through a dental restoration removing instrument on which the wrench is employed in accordance with a preferred embodiment of the subject invention.

To this end, and by way of example, the upper portion of the sleeve 32 may be provided with an integral or firmly attached collar 41 which, as seen in FIGS. 5, 7 and 12, has two lands or flat lateral portions 42 and 43 for engagement by prongs 44 and 45 of a wrench 46. This wrench has a manually engageable handle 47, only part of which is visible in the drawings.

In practice, the wrench is held by the dentist in such a position that the previously rotated projections 38 and 39 remain below and in engagement with the shelves 23 and 24 of the restoration 12.

It will now be recognized that the inserted and actuated instrument 31 with lateral projections 38 and 39 establishes at the aperture 18 a force or forces acting on the shelves 23 and 24 relative to and away from the tooth 10, and that the restoration 12 is removed from the tooth with that force or those forces. In principle, a single extension 38 and a single undercut shelf 24 could be employed for establishing at the aperture 18 a force acting on the shelf relative to and away from the tooth for a removal of the restoration 12. However, the illustrated embodiment wherein two diametrically opposed projections 38 and 39 engage corresponding undercut portions or shelves of the dental restoration is presently preferred.

In accordance with a further preferred embodiment of the subject invention, the tip of the screw 33 is provided with a foot 49 for engaging the tooth or dental matter. If the screw tip 34 has a given first diameter, then the foot 49 connected to that tip is larger than that first diameter. For instance, the foot 49 may have a diameter equal to the diameter of the sleeve 34 since the small width 21 is wide enough to accommodate the sleeve 32.

The larger effective area of the foot 49 as compared to the cross-section of the tip 34 distributes the force exerted on the tooth 10 over a larger area, thereby further inhibiting a splitting of or other damage to the tooth by the illustrated instrument. This favorably distinguishes the action of the dental instrument of the subject invention from the action of the above mentioned screw-type remover which necessarily has a relatively sharp tip on the conical tapping screw engaging and often splitting the tooth structure. Even the screw tip 34 of FIGS. 5, 7 and 11 is better than the tip of the prior-art tapping screw in preventing splitting of the tooth structure.

Figure 11:
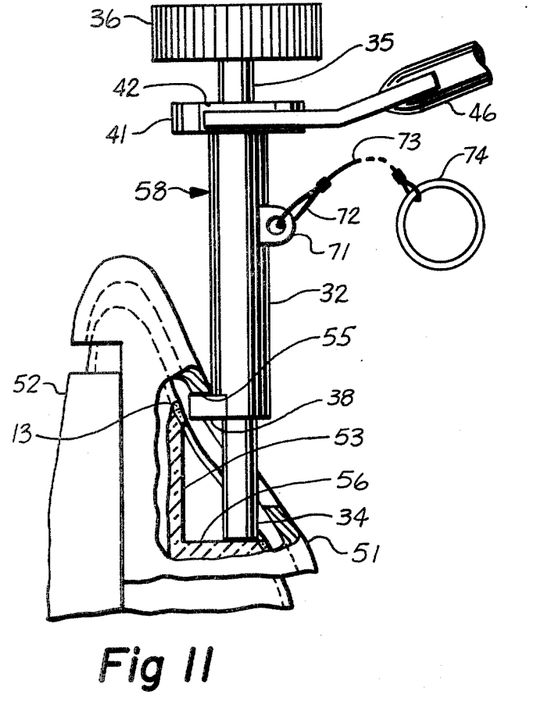
FIG. 11 is an elevation of a dental restoration removing instrument in accordance with a preferred embodiment of the subject invention, together with a detail view, on an enlarged scale, of the tooth shown in FIGS. 9 and 10 upon removal of the dental restoration from the tooth.

FIGS. 9 to 11 show the removal of a partial crown 51 from an incisor or canine tooth 52. The same principle is applicable for removing a partial crown from a molar or premolar or for removing a lateral inlay or onlay or similar bridge abutments from any tooth.

According to FIGS. 9 and 10 an aperture 53 is provided in a side wall of the restoration 51 and is extended into dental matter or tooth adjacent the restoration. The previously mentioned drill 15 driven by the turbine 16 may be employed for cutting the aperture 53.

In particular, the drill 15 with turbine 16 may be employed to provide in the dental restoration 51 and in the tooth 52 or dental matter below the restoration the aperture 53 and, respectively, first and second lands 55 and 60 facing each other across the aperture 53. The aperture thus has a first land 55 located on a top portion of the aperture 53 in the restoration 51 and a second land 56 located on a bottom portion of the aperture 53 in the tooth 52.

A dental instrument 58 according to a further preferred embodiment of the subject invention is then employed as seen in FIG. 11 to establish at the aperture 53 a force acting on the restoration 51 and between the first and second lands 55 and 56, and for removing the restoration 51 from the tooth 52 with that force.

As seen from a comparison of FIGS. 5 and 11, the dental instrument 58 may be similar to the previously described instrument 31, with like reference numerals among the instruments 31 and 58 designating like or functionally equivalent parts. According to FIG. 11, the dental instrument 58 only has one projection 38, since it needs only one such projection for engaging the dental restoration 51 at the land 55. As seen in FIG. 11, the projection 38 extends to the approximate thickness of the partial crown 51.

However, a second projection 39 may be provided on the instrument 58 in the manner of the projection 39 shown in FIG. 5, or the instrument 31 may be employed in lieu of the instrument 58 is removing the lateral dental restoration 51.

Accordingly, after the lateral aperture 53 has been formed as shown in FIGS. 9 and 10, the dental instrument 31 or 58 is inserted so that the projection 38 engages the land 55 of the restoration 51 and the screw tip 34 engages the land 56 in the dental structure. The wrench 56 may again be employed on the collar 51 to restrain the sleeve 32 against rotation when the knob 36 is rotated relative to the sleeve 32 to extend the screw tip 34 relative to the sleeve 32 and projection 38.

Continued rotation of the knob 36 establishes at the aperture 53 a force acting on the restoration 51 and between a wall of that aperture in the restoration at a side wall of the extended aperture in the tooth structure or dental matter at 56. In consequence, the bond or cement layer between the restoration 51 and tooth 52 is broken and the restoration 51 is removed from the tooth with the force generated by the instrument 58 as shown in FIG. 11.

Figure 13:
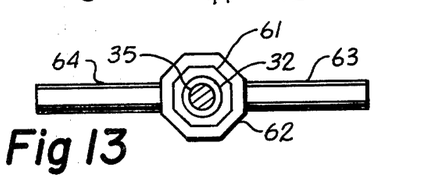
FIG. 13 is a top view of a further wrench, together with a section of a dental restoration removing instrument on which it is employed in accordance with a further preferred embodiment of the subject invention.
Figure 14:
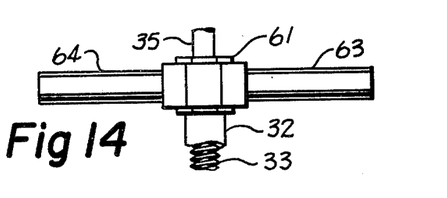
FIG. 14 is a side view of the wrench and partially shown restoration removing instrument of FIG. 13.

As shown in FIGS. 13 and 14, the collar 41 may be replaced by a hexagonal collar 61 which is integral with or attached to the sleeve 32. That collar 61 is engaged by a hexagonal wrench 62 which has one or two handles 63 and 64.

The combination of hexagonal collar 61 and hexagonal wrench 62 may be employed in either dental instrument 31 and 58 and tends to afford a somewhat better control of the restraint against rotation of the sleeve 32 than a two-pronged wrench.

If desired, the knob 36 may be given a hexagonal shape similar to the shape of the collar 61 and a hexagonal wrench similar to the wrench 62 may then be employed to rotate the shaft 35 relative to the sleeve 32. If desired, such wrench may be configured or actuated in the manner of a wing nut.

A review of FIGS. 1 to 14 shows that the preferred embodiments of the subject invention therein shown, as a unifying feature, provide an aperture in a dental restoration 12 or 51 for receiving first and second parts of a dental instrument 31 or 58. By way of example, the first part of either instrument 31 and 58 includes at least the projection 38, and the second part includes at least the tip 34. Either aperture 18 or 53 is extended into dental matter adjacent the restoration 12 or 51. The particular restoration is engaged at the aperture 18 or 53 with the first part 38 of the dental instrument 31 or 58. The second part 34 of the dental instrument is moved against dental matter in the extended aperture relative to the first part 38 to remove the restoration from the tooth as shown in FIG. 7 and also in FIG. 11.

Preparatory to and in the course of this removal, the restoration 12 or 51 is engaged at the aperture 18 or 53 with the lateral projection 38 of the first part of the dental instrument 31 or 58.

Considering FIGS. 5, 7 and 11, it should be recognized that the inserted and applied dental instrument 31 and 58 in effect forms a combination with the restoration 12 and 51 and that the operation of such combination results in the desired removal of the restoration 12 or 51. In a preferred embodiment of such combination, the parts 32, 35, 36 and 41, if desired, serve as means connected to the first and second parts 38 and 34 for moving such parts relatively to each other whereby to remove the restoration from the tooth.

FIG. 11 shows a further feature which may be employed with either dental instrument 31 and 58.

In particular, the casing or sleeve 32 in FIG. 11 has an integral or firmly attached eye 71. A loop 72 of a line 73 extends through the eye at one end of the line. A ring or other engageable member 74 is attached to the other end of the line. In practice, the combination of elements 71 to 74 is employed as a means for restraining the instrument 31 or 58 against gravitational force in case the instrument should dislodge itself and drop into the patient's oral cavity. If desired, the loop 72 of the line 73 may extend around the shaft 35. The line 73 is thus directly or indirectly connected to at least one of the above mentioned first and second parts for restraining such parts or the dental instrument against gravitational force or against entry of the patient's throat.

If desired, a removed dental restoration may again be applied to the tooth. For instance, an aperture 18 or 53 in a removed restoration may be closed by soldering or by another desired technique in the dental lab. Alternatively, an aperture 18 or 53 may be filled by the dentist after the restoration has been reapplied to the tooth.

The subject extensive disclosure will render apparent or suggest to those skilled in the art various modifications and variations within the spirit and scope of the subject invention.

I claim:

1. A method of removing a dental restoration from a tooth, comprising in combination the steps of:
    providing an instrument with lateral projection means at a lower portion thereof;
    providing an aperture in and through the restoration;
    extending said aperture into an oblong shape in a face of the restoration by providing said aperture with a sufficient first width in said restoration for a reception of said projection means therethrough, and a second width extending in the same plane as said first width at an angle to said first width and being too small to receive said projection means;
    establishing part of the restoration at the aperture as a shelf facing in the direction of the tooth by undercutting beneath the restoration at said aperture in extension of said second width;
    inserting said lower portion of the instrument into said oblong aperture, with said lateral projection means being oriented in alignment with said first width of said oblong aperture and being inserted to below said dental restoration;
    rotating said lateral projecting means for moving said lateral projection means to below said shelf;
    establishing at the aperture with said lateral projection means a force acting on the shelf relative to and away from the tooth; and
    removing the restoration from the tooth with said force.

2. A method of removing from a tooth a dental restoration located on dental matter including said tooth, comprising in combination the steps of:
    providing an aperture in the restoration;
    extending said aperture into dental matter adjacent the restoration;
    establishing at the aperture a force acting on the restoration and between a wall of said aperture in the restoration and a side wall of said extended aperture in dental matter; and
    removing the restoration from the tooth with said force.

3. A method as claimed in claim 2, wherein:
    said restoration is located on a side of said tooth;
    said aperture is provided on said side of the tooth and is extended into dental matter from said side; and
    said force for removing the restoration is provided as a net force extending away from the tooth at an angle to said side.

4. A method of removing from a tooth a dental restoration having a side wall and being located on said tooth, comprising in combination the steps of:
    providing in said side wall of the dental restoration and in an adjacent portion of said tooth an aperture having a first land located on a top portion of said aperture in the restoration and a second land located on a bottom portion of the aperture in said tooth;
    establishing at the aperture a force acting on the restoration and between the first and second lands; and
    removing the restoration from the tooth with said force.

5. A method of removing a dental restoration from a tooth, comprising in combination the steps of:

providing an instrument with lateral projections at a lower portion thereof;

providing an aperture in and through the restoration;

extending said aperture into an oblong shape in a face of the restoration by providing said aperture with a sufficient first width in said restoration for a reception of said projections therethrough, and a second width extending in the same plane as said first width at an angle to said first width and being too small to receive said projections;

establishing a first portion of the restoration at the aperture as a first shelf facing in the direction of the tooth, and a second portion of the restoration across the aperture from the first part as a second shelf facing in the direction of the tooth by undercutting the restoration at said aperture in extension of said second width;

inserting said lower portion of the instrument into said oblong aperture, with said lateral projections being oriented in alignment with said first width of said oblong aperture and being inserted to below said dental restoration;

rotating said instrument for moving said lateral projections to below said shelves;

establishing at the aperture with said lateral projections forces acting on the first and second shelves relative to and away from the tooth; and removing the restoration from the tooth with said forces.

6. A method as claimed in claim 5, including the step of:

providing said first and second shelves as diametrical extensions of said smaller second width.

7. A method of removing a dental restoration from a tooth with the aid of an instrument having relatively movable first and second parts comprising in combination the steps of:

providing said first part with a lateral projection;

providing an aperture in and through the restoration for receiving the first and second parts;

extending said aperture into an oblong shape in a face of restoration by providing said aperture with a sufficient first width in said restoration for a reception of said first and second parts along with said lateral projection, and a second width extending in the same plane as said first width at an angle to said first width and being too small to receive said lateral projection along with the first and second parts;

undercutting the restoration at the aperture in extension of said second width;

inserting the first part with lateral projection and the second part into the aperture through said first width and moving the projection of the first part into line with the second width and under the undercut restoration; and moving the inserted second part against the tooth and relative to the first part to remove the restoration from the tooth.

8. A method of removing from a tooth with the aid of an instrument, having a first part and a second part, a dental restoration having a side wall and being located on said tooth, comprising in combination the steps of:

providing an aperture in said side wall of the restoration and in a portion of said tooth adjacent the restoration, and providing said aperture with a first land located on a top portion of said aperture in the restoration and a second land located on a bottom portion of the aperture in said tooth;

engaging the restoration at said first land of the aperture with the first part of said instrument; and moving the second part of said instrument against said tooth at said second land of the aperture and relative to the first part to remove the restoration from the tooth.

9. A method as claimed in claim 8, including the steps of:

providing the first part with a lateral projection; and engaging the restoration at said first land of the aperture with the lateral projection of the first part.

10. A method of removing a dental restoration from a tooth with the aid of an instrument having relatively movable first and second parts said dental restoration being affixed to said tooth by a cement layer, comprising in combination the steps of:

providing the first part of the instrument with lateral projections extending in opposite directions and corresponding in thickness to said cement layer;

providing the restoration with an aperture having a first width for receiving the first and second parts along with said lateral projections, and having a second width extending at an angle to the first width and being too small to receive said lateral projections along with the first and second parts;

undercutting the restoration in extension of the second width;

inserting the first part with said lateral projections and the second part through the first width of the aperture;

positioning the lateral projections under the undercut restoration at opposite extensions of the second width of the aperture;

moving the inserted second part against the tooth and the positioned lateral projections into engagement with the restoration; and removing the restoration from the tooth by moving the inserted first and second parts relatively to each other.

11. A method as claimed in claim 10, wherein:

said first and second parts are inserted into the aperture with said lateral projections aligned with the first width; and said lateral projections are positioned under the undercut restoration by rotating the first and second parts and angularly moving the lateral projections from alignment with the first width into alignment with the second width.

12. A dental instrument for removing from a tooth a partial crown having a side wall and an aperture extending into the tooth, comprising in combination:

a first part having a lateral projection extending to the approximate thickness of said partial crown for engaging the partial crown at the aperture, a second part extending through said first part for engaging the tooth at the aperture and having thread means engaging said first part, and means connected to the first and second parts for rotating the second part relative to the first part while maintaining said first part against rotation whereby to remove the restoration from the tooth.

13. A dental instrument for removing from a tooth a dental restoration affixed to said tooth by a cement layer and having an oblong aperture of a first width and a second width extending in the same plane as the first width at an angle to and being smaller than said first width, comprising in combination:
- means for establishing at the aperture a force acting on the restoration in a direction away from the tooth, including a first part insertable into the aperture and having lateral projections corresponding in thickness to said cement layer and having an overall dimension smaller than said first width and larger than said second width for insertion of said first part and lateral projections through said oblong aperture in alignment with said first width and for engaging the restoration upon alignment of said lateral projections with said second width after insertion of said lateral projections to below the restoration;
- a second part extending through said first part for engaging said tooth below said restoration and having thread means engaging said first part; and
- means connected to the first and second parts for rotating the second part relative to the first part while maintaining said first part against rotation to remove the restoration from the tooth.

14. A dental instrument as claimed in claim 13, wherein: said first and second lateral projections are located at opposite sides of the first part for engaging the restoration at opposite sides of the aperture.

15. A dental instrument as claimed in claim 13, wherein:
said second part includes a screw having a foot for engaging the tooth.

16. A dental instrument as claimed in claim 13, wherein:
said second part has a tip having a first diameter; and
said second part has a foot connected to said tip and being larger than said first diameter.

17. A dental instrument as claimed in claim 13, including:
means connected to the second part for rotating the second part relatively to the first part;
means connected to the first part for restraining rotation of the first part during rotation of the second part relatively to the first part; and
means connected to the first and second parts for translating rotation of the second part relative to the first part into translatory motion of the second part relative to the first part.

18. A dental instrument as claimed in claim 13, including:
means connected to at least one of said first and second parts for restraining said parts against gravitational force.

* * * * *